United States Patent [19]

Salinero-Rodero et al.

[11] Patent Number: 5,284,873

[45] Date of Patent: Feb. 8, 1994

[54] PHARMACEUTICAL COMPOSITIONS DERIVED FROM THE ACID FRACTION OF LIPID EXTRACTS OF SABAL SERRULATA, WITH ADRENERGIC ANTAGONIST ACTIVITY AND METHOD OF PREPARING SAID COMPOSITION

[75] Inventors: Miguel-Angel Salinero-Rodero, Peñaranda; Ma-Angeles Sevilla-Toral, Salamanca; José-Ma Miguel-del-Corral, Salamanca; Ma-José Montero-Gómez, Salamanca; Arturo San-Feliciano-Martin; Luis San-Román-del-Barrio, both of Santa Marta; José-Antonio Poch-Gabarró; Antonio Mañes-Armengol, both of Barcelona, all of Spain

[73] Assignee: Laboratorios Madaus-Cerafarm, S.A., Barcelona, Spain

[21] Appl. No.: 911,613

[22] Filed: Jul. 10, 1992

[30] Foreign Application Priority Data

Jul. 11, 1991 [ES] Spain .................................. P9101710

[51] Int. Cl.$^5$ ............................................. A61K 31/20
[52] U.S. Cl. ..................................... 514/558; 514/886
[58] Field of Search ..................... 424/195.1; 514/552, 514/557, 558, 886

[56] References Cited

FOREIGN PATENT DOCUMENTS

| 394117 | 7/1970 | European Pat. Off. |
|---|---|---|
| 0068055 | 1/1983 | European Pat. Off. ...... A61K 35/78 |
| 8500622 | 7/1983 | European Pat. Off. ...... C07G 17/60 |
| 0265338 | 4/1988 | European Pat. Off. ...... C07G 17/60 |
| 0287000 | 10/1988 | European Pat. Off. ...... A61K 35/78 |
| 2480754 | 10/1981 | France ......................... A61K 35/78 |

OTHER PUBLICATIONS

The Merck Index, 9th Ed, 1976, II 8582, 6805, 6674, 6160, 5343, 5344, 5230, 792, 1764.
Chem. Abst. 110:209328x, 1989.
Japan Patent Information Organization (JAPIO), 85-21508, Oct. 1985.

*Primary Examiner*—John W. Rollins
*Attorney, Agent, or Firm*—Cushman, Darby & Cushman

[57] ABSTRACT

The new compositions of the invention are formed by the total acid fraction obtained by alkali hydrolysis of the lipid extracts of the fruit of Sabal serrulata. Said compositions have an effective adrenergic antagonist action and a complementary antiinflammatory action, together with a high degree of innocuity and slight side effects, making its use highly effective for combatting prostate affections and, more particularly, benign hypertrophy of the prostate.

9 Claims, No Drawings

PHARMACEUTICAL COMPOSITIONS DERIVED FROM THE ACID FRACTION OF LIPID EXTRACTS OF SABAL SERRULATA, WITH ADRENERGIC ANTAGONIST ACTIVITY AND METHOD OF PREPARING SAID COMPOSITION

FIELD OF THE INVENTION

The present invention relates to new compositions having pharmacological applications with an $\alpha$-adrenergic receptor antagonist action, consisting of a mixture of fatty acids which may be obtained by alkali hydrolysis of the lipid extracts of the Sabal serrulata fruit, as well as a process for the preparation thereof.

STATE OF THE ART

It has been known for some time now that the extracts of the fruit of the Sabal serrulata palm tree, also known as Serenoa repens, have a beneficial activity in the treatment of affections of the prostate gland and that they have a particularly outstanding application in the case of Benign Prostate Hypertrophy (BPH).

It is also known, as described in the American Pharmacopoeia (National Formulary VII, 137 and VIII, 457), that these extracts may be prepared in aqueous alcoholic tincture form by extraction of the fruit of said plant with 80% vol. aqueous alcohol. Nevertheless, said tinctures, together with the lipid components responsible for the antiprostate action contain appreciable amounts of hydrophilic components not having such action. Consequently, several processes have been developed for preparing the lipid extracts, such as those described in French patent No. 2 480 754 (equivalent to Spanish patent No. 501,429), Belgian patent No. 1 000 036 and EP-A- 0 250 953.

EP-A-0 287 000 teaches that the antiandrogenic activity of the lipid extracts of Sabal serrulata is bound to the alcohol fraction thereof, considering that the fatty acid fraction is substantially lacking of such action. The technique disclosed by that patent has the drawback that, since the alcoholic fraction is clearly a minority component of the lipid extract, a large amount of plant material is required to obtain small amounts of active substance.

Furthermore, the prostate tissue is known to be rich in $\alpha$-adrenergic receptors and that treatment of the $\alpha$-receptors with antagonists, such as phenoxybenzamine or prazosin, brings about an effective improvement in prostate patients.

Contrary to what is to be expected from the description of the above mentioned EP-A-0 287 000, the present inventors have surprisingly found that the total fatty acid fraction of Sabal serrulata extract, i.e. the ensemble of the free fatty acids plus those obtained from hydrolysis of the esters (hereinafter total acid fraction, TAF) has a potent $\alpha$-adrenergic receptor blocking action and, consequently, they have a potential application both in the treatment of BPH and of other disorders in which it is desirable to block such receptors. Said total acid fraction, being a majority component of the plant lipid extract, may be prepared with very good yields by weight from the fruit thereof.

SUMMARY OF THE INVENTION

The object of the invention, therefore, is to provide a new $\alpha$-adrenergic receptor blocking agent, consisting of the total acid fraction of the Sabal serrulata lipid extracts.

A further object of the present invention is to prepare pharmaceutical compositions for the treatment of affections of the prostate gland based on said total acid fraction of Sabal serrulata lipid extracts.

Yet a further object of the invention is to provide a process for the preparation of said total acid fraction.

DESCRIPTION OF THE INVENTION

As said above, the total acid fraction (TAF) which may be obtained from the lipid extracts of Sabal serrulata is formed essentially by the ensemble of the free fatty acids plus the fatty acids from ester hydrolysis.

The TAF of the invention is a yellowish oily liquid having the characteristic odour of the mother plant. It is insoluble in water but soluble in ethanol, hexane, hydrocarbons, halogenated hydrocarbons, esters, ethers, etc and has the following physical and chemical properties:

Density at 20° C.: 0.885–0.895
Weight loss on desiccation: less than 5%
Refractive index n D/20: 1.44–1.46
Saponification number: 215–230
Acid number: 215–230
Iodine number: 39–45
Fatty acid content (gas chromatography expressed as wt % of total):

| | |
|---|---|
| Total content: | 95–98% |
| Caprylic | 1.0–1.3% |
| Capric | 1.0–2.0% |
| Lauric | 21–25% |
| Myristic | 11–12% |
| Palmitic | 10–11% |
| Palmitoleic | 0.1–0.3% |
| Stearic | 1.5–2.5% |
| Oleic | 38–43% |
| Linoleic | 1.8–3% |
| Linolenic | 0.5–1.0% |
| Arachic | 0.05–0.20% |
| Eicosenoic | 0.01–0.2% |

The extract contains further other minor components such as:
Unsaponifiables: less than 0.5%
Esters: less than 0.1%
Sterols: less than 0.2%
Aliphatic alcohols: less than 0.1%

The $\alpha$-adrenergic receptor antagonist action has been checked by organ bath tests, in which an $\alpha$-adrenergic receptor agonist, such as noradrenaline, has been added, using tissues of different biological sources among which the following may be named:
vas deferens of the rat
electrically stimulated vas deferens of the rat
potassium depolarized vas deferens of the rat
rabbit and guinea pig urethra
human prostate gland It is gathered from said tests that the $\alpha$-blocking action of the TAF is non competitive, which is a considerable advantage from the clinical point of view since it means a reduction of undesirable side effects, such as hypotensive effects proper to the competitive antagonists.

On the other hand, it may be established from the observation of the relationship between the dose levels used and the effect obtained that the action of the TAF is dose dependent, i.e., the larger the dose the greater the blocking effect.

It has been demonstrated that the α-adrenergic receptor blocking action is bound fundamentally to the acid fraction of the Sabal serrulata lipid extract, since neither the esterified fraction nor the unsaponifiable fraction have any significant activity in this respect. It has also been shown experimentally that the TAF has a marked antiinflammatory effect which, together with its adrenergic antagonistic effectiveness, makes it particularly efficacious for combatting the symptomatology of benign hypertrophy of the prostate.

The process of preparing the TAF consists essentially of preparing an essentially lipid extract of the fruit of the Sabal serrulata, followed by saponifying the extract in an alkali aqueous medium, removing the unsaponifiables by solvent extraction and, after releasing the fatty acids from the alkali salts thereof by addition of acid to an appropriate pH, extracting the total acid fraction with an appropriate solvent, followed by purification by removal of the solvent and decolouring the oily residue.

The lipid extract of the Sabal serrulata fruit may be prepared in any known way, although a method using water and ethanol as solvents, as described hereinafter, is preferred because of its simplicity and lower industrial risk.

The ground fruit of the plant is exhaustively extracted with water at a temperature ranging from 80° to 100° C. The extraction liquor, which has dissolved the hydrophilic components, is rejected and the marc, containing the lipid components, is extracted in turn with 96 vol.-% ethanol, with heating to a temperature ranging from ambient to just below the boiling point of the solvent. After removal of the extraction marc, the ethanol is concentrated at a reduced pressure of below 50 mm Hg and at a temperature ranging from ambient to 60° C.

The thus obtained ethanolic concentrate is used directly in the saponification step.

Saponification may be carried out by heating the extract to reflux in a dilute aqueous solution of a strong base such as, for example, sodium or potassium hydroxide or in a concentrated aqueous solution of a weaker base, such as, for example, sodium or potassium carbonate, ammonia, etc.

The unsaponifiable fraction is removed by extraction of the mixture from the saponification with an appropriate non-polar solvent such as hexane, ethyl acetate, diethyl ether, halogenated hydrocarbons, etc.

The aqueous phase resulting from the previous step is acidulated with a mineral acid to pH below 4 and the acid fraction is extracted with a non polar solvent such as those described above.

Removal of the said solvent and the possible decolouring of the oily residue obtained provide the total acid fraction (TAF), having the above mentioned physical and chemical properties and a remarkable α-adrenergic receptor blocking action.

All kinds of pharmaceutical preparations may be obtained from the thus prepared TAF. Thus, the TAF may be adsorbed on inert substrates, such as for example, silica, inorganic complexes, etc. for subsequent formulation in solid pharmaceutical forms such as tablets, pills, hard gelatine capsules, etc. Liquid pharmaceutical preparations may also be obtained in the form of emulsions, soft gelatine capsules, etc.

The following EXAMPLES are given for a better understanding of the technical features of the invention, without that they should be understood as limiting the invention:

EXAMPLE 1

A reactor provided with stirrer was charged with 100 kg of ground Sabal serrulata fruit. 1,000 liters of water were added and heated to 85° C. with stirring over 1 hour. The aqueous phase was discarded and the marc was extracted again under the same conditions with a further 1,000 liters of water, which were also discarded. 1,000 liters of 96 vol % ethanol were added over the marc or residual drug in the same reactor and were stirred for 1 hour while holding the temperature at 50° C. The ethanolic phase was removed and the marc was extracted again under the same conditions with a further 1,000 liters of 96 vol % ethanol. The marc from the second extraction was discarded and the two alcoholic solutions obtained were pooled in a reactor equipped for low pressure distillation in which the alcohol solution was concentrated at a temperature of 50° C. and with an appropriate vacuum until the alcoholic solution had approximately a 20% dry material content, equivalent to 10–15 kg of dry extract. An aqueous solution formed by 3.36 kg of potassium hydroxide dissolved in 13.5 liters of water was added to the alcoholic solution and was heated to reflux with stirring for 4 hours. Thereafter, the mixture was stirred at ambient temperature for 24 hours. The resulting solution was extracted with tetrachloroethylene, once at a 5:1 ratio and three times at 2.5:1. The dense chlorinated solvent phases containing the unsaponifiable fraction were discarded and the light aqueous alcoholic phase was acidulated with sulphuric acid to pH 3.5. The acid fraction was extracted twice at a volumetric ratio of 2.5:1 with tetrachloroethylene, the light aqueous alcoholic phase being discarded. Both tetrachloroethylene phases were pooled and washed several times with water until the residual acidity had been removed. The tetrachloroethylene solution was concentrated under vacuum at 50° C. until removal of the solvent, the residue was thereafter decoloured with 0.4 kg of activated carbon and 1.5 g of thyme extract were added as natural antioxidant. The residue was finally dried at a reduced pressure of 15 mm Hg, at 60° C., until the last traces of solvent were removed, leaving 7 to 11 kg of purified total acid fraction having physical and chemical properties similar to those mentioned in the description.

EXAMPLE 2

The α-adrenergic receptor blocking action of the total acid fraction obtained in Example 1 was determined by testing on the vas deferens of the rat.

A sufficient amount of noradrenaline to provoke the maximum degree of contraction of the rat vas deferens tissue was used as agonist. The determinations were carried out in an organ bath at physiological temperature and were compared with a control to which the acid fraction had not been added and with a sample of the unsaponifiable fraction (UF) of the Sabal serrulata lipid extract.

The maximum extinction levels ($E_{max}$) corresponding to the percentage of tissue contraction relative to the maximum contraction of the control were determined. The values obtained, representing the statistical mean of various tests, are given in the following Table:

| Sample | Concentration (mg/ml) | $E_{max}$ (%) |
|---|---|---|
| Control | — | 100.0 |
| UF | 0.8 | 95.0 |

-continued

| Sample | Concentration (mg/ml) | $E_{max}$ (%) |
|---|---|---|
| TAF | 0.4 | 84.2 |
| TAF | 0.8 | 41.5 |

It may clearly be gathered from the data of the Table that the unsaponifiable fraction does not bring about a significant reduction of the contraction and, therefore, does not have any α-adrenergic blocking action.

In contrast, the total acid fraction produces a substantial relaxation of the fibre at low concentrations and at higher concentrations produces a potent antiadrenergic relaxing action.

EXAMPLE 3

The adrenergic receptor blocking activity of the TAF prepared according to Example 1 was determined in the same way as in Example 2, using human prostate tissue, with the following results:

| Sample | Concentration (mg/ml) | $E_{max}$ (%) |
|---|---|---|
| Control | — | 100.0 |
| TAF | 0.8 | 66.9 |

A significant reduction of the tissue contraction relative to the control has obviously occurred.

EXAMPLE 4

The antiinflammatory action of the TAF prepared according to Example 1 was shown by the following tests:
A) carrageenin test on rat paw and
B) histamine increased capillary permeability, using oral and parenteral administration in both cases.

The percentage inhibition of the inflammation was determined between three and five hours using indomethacin and dexamethasone as reference substances.

Dosages of 100, 250 and 500 mg/kg i.p. and 750 mg/kg oral were tested, with the following results:

| Intraperitoneal | $ED_{50}$ (method A) (mg/kg) | $ED_{50}$ (method B) (mg/kg) |
|---|---|---|
| TAF | 148.66 ± 12.17 | 181.31 |

$ED_{50}$ is the effective dose inhibiting 50% of the inflammation.

| Oral | Dose | % inhibition (method A) |
|---|---|---|
| TAF | 750 mg/kg | 39.39 ± 5.68% |

These results confirm that the TAF, administered in both ways, reduces the oedema with similar $ED_{50}$ values in both tests.

EXAMPLE 5

Tests were performed on anaesthetized normal tension rats to check the absence of side effects on the arterial pressure and on the heart rate, by administering TAF intraduodenally at three dose levels, 180, 270 and 360 mg/kg corresponding to dosages of 2, 3 and 4 g in man.

Under these experimental conditions, at dosages of 180 and 270 mg/kg, the TAF does not induce modifications of the blood pressure or of the heart rate different from those observed in the control group. At a dosage of 360 mg/kg, the treated animals had a slight hypertension, although without statistically significant differences over those observed in the control group.

EXAMPLE 6

Acute toxicity tests ($LD_{50}$) were performed on the rat and the mouse and subacute toxicity tests on the rat and Beagle dog.

Oral $LD_{50}$ of TAF, both in the mouse and in the rat is in excess of 4,000 mg/kg.

The results of subacute toxicity for TAF administered orally for four weeks are as follows:

| Animal | Dose (mg/kg) | Deaths |
|---|---|---|
| Rat | 1000 | 0 |
| Rat | 2000 | 0 |
| Rat | 4000 | 0 |
| Beagle dog | 3000 | 0 |
| Beagle dog | 4000 | 0 |

The acute and subacute innocuity of TAF is thus shown in these tests.

We claim:

1. Pharmaceutical composition obtained by alkali hydrolysis of the lipid fraction of the extracts of the fruit of Sabal serrulata and separation of the total acid fraction (TAF), said composition comprising a mixture of fatty acids in the proportion, expressed as a weight percentage, in accordance with their gas chromatography analysis,

| | |
|---|---|
| Caprylic | 1.0–1.3% |
| Capric | 1.0–2.0% |
| Lauric | 21–25% |
| Myristic | 11–12% |
| Palmitic | 10–11% |
| Palmitoleic | 0.1–0.3% |
| Stearic | 1.5–2.5% |
| Oleic | 38–43% |
| Linoleic | 1.8–3% |
| Linolenic | 0.5–1.0% |
| Arachic | 0.05–0.20% |
| Eicosenoic | 0.01–0.2%, | together with an amount of less than 0.5 wt % of unsaponifiables and less than 0.1 wt % of fatty acid ethers.

2. The pharmaceutical composition of claim 1, wherein said composition includes the following physico-chemical properties:

| | |
|---|---|
| Density at 20° C.: | 0.885–0.895 |
| Weight loss on desiccation: | less than 5% |
| Refractive index n D/20: | 1.44–1.46 |
| Saponification number: | 215–230 |
| Acid number: | 215–230 |
| Iodine number: | 39–45 |

3. Pharmaceutical preparation comprising as one of the active ingredients, a composition obtained by alkali hydrolysis of the lipid fraction of the extracts of the fruit of Sabal serrulata and separation of the total acid fraction (TAF), said composition being a mixture of fatty acids in the proportion, expressed as a weight percentage, in accordance with their gas chromatography analysis,

| | |
|---|---|
| Caprylic | 1.0–1.3% |
| Capric | 1.0–2.0% |
| Lauric | 21–25% |
| Myristic | 11–12% |
| Palmitic | 10–11% |
| Palmitoleic | 0.1–0.3% |
| Stearic | 1.5–2.5% |
| Oleic | 38–43% |
| Linoleic | 1.8–3% |
| Linolenic | 0.5–1.0% |
| Arachic | 0.05–0.20% |
| Eicosenoic | 0.01–0.2% | together with an amount of less than 0.5 wt % of unsaponifiables and less than 0.1 wt % of fatty acid esters.

4. The pharmaceutical preparation of claim 3, further including a pharmaceutically acceptable carrier.

5. The process of claim 4, wherein the lipid extract is obtained by grinding said Sabal serrulata fruit and removing the hydrophilic components by extraction of the lipids from the fruit, employing hot water and subsequent extraction thereof with 96 vol % ethanol.

6. The process of claim 5, wherein the total acid fraction obtained comprises less than 0.5 wt % of unsaponifiables and less than 0.1 wt % of fatty acid esters.

7. A process for the preparation of the total acid fraction of the lipid extract of Sabal serrulata fruit comprising the following steps:
   saponifying said lipid extract in an alkali aqueous medium;
   removing the unsaponifiable fraction by extraction with non-polar solvents;
   acidulating the aqueous phase with mineral acids; and
   extracting the total acid fraction employing non-polar solvents.

8. A method of treating hypertrophy of the prostate which comprises administering to a patient in need of such treatment a therapeutically effective amount of a composition obtained by alkali hydrolysis of the lipid fraction of the extracts of the fruit of Sabal serrulata and separation of the total acid fraction (TAF), said composition comprising a mixture of fatty acids in the proportion, expressed as a weight percentage, in accordance with their gas chromatography analysis,

| | |
|---|---|
| Caprylic | 1.0–1.3% |
| Capric | 1.0–2.0% |
| Lauric | 21–25% |
| Myristic | 11–12% |
| Palmitic | 10–11% |
| Palmitoleic | 0.1–0.3% |
| Stearic | 1.5–2.5% |
| Oleic | 38–43% |
| Linoleic | 1.8–3% |
| Linolenic | 0.5–1.0% |
| Arachic | 0.05–0.20% |
| Eicosenoic | 0.01–0.2% | together with an amount of less than 0.5 wt % of unsaponifiables and less than 0.1 wt % of fatty acid esters.

9. A method of treating inflammation which comprises administering to a patient in need of such treatment a therapeutically effective amount of a composition obtained by alkali hydrolysis of the lipid fraction of the extracts of the fruit of Sabal serrulata and separation of the total acid fraction (TAF), said composition comprising a mixture of fatty acids in the proportion, expressed as a weight percentage, in accordance with their gas chromatography analysis,

| | |
|---|---|
| Caprylic | 1.0–1.3% |
| Capric | 1.0–2.0% |
| Lauric | 21–25% |
| Myristic | 11–12% |
| Palmitic | 10–11% |
| Palmitoleic | 0.1–0.3% |
| Stearic | 1.5–2.5% |
| Oleic | 38–43% |
| Linoleic | 1.8–3% |
| Linolenic | 0.5–1.0% |
| Arachic | 0.05–0.20% |
| Eicosenoic | 0.01–0.2% | together with an amount of less than 0.5 wt % of unsaponifiables and less than 0.1 wt % of fatty acid esters.

* * * * *